US008083099B2

(12) United States Patent
Meyer et al.

(10) Patent No.: US 8,083,099 B2
(45) Date of Patent: Dec. 27, 2011

(54) METHOD AND DEVICE FOR PRODUCING A MULTICOMPONENT COMPOUND

(75) Inventors: Sven Meyer, Apensen (DE);
Hans-Dieter Höhnk, Reinbek (DE);
Matthias Weihrauch, Klein Nordende (DE)

(73) Assignee: Ernst Muhlbauer GmbH & Co. KG, Norderfriedrichskoog (DE)

( * ) Notice: Subject to any disclaimer, the term of this patent is extended or adjusted under 35 U.S.C. 154(b) by 858 days.

(21) Appl. No.: 11/988,815

(22) PCT Filed: Jun. 14, 2006

(86) PCT No.: PCT/EP2006/005735
§ 371 (c)(1),
(2), (4) Date: Jan. 15, 2008

(87) PCT Pub. No.: WO2007/009537
PCT Pub. Date: Jan. 25, 2007

(65) Prior Publication Data
US 2009/0145921 A1    Jun. 11, 2009

(30) Foreign Application Priority Data

Jul. 15, 2005  (DE) .................. 10 2005 033 261

(51) Int. Cl.
*B67D 7/78* (2010.01)
(52) U.S. Cl. ........... 222/1; 222/63; 222/145.6; 222/137; 222/333; 433/89; 73/199

(58) Field of Classification Search .............. 222/1, 63, 222/137, 145.5–145.6, 333; 73/199; 433/89
See application file for complete search history.

(56) References Cited

U.S. PATENT DOCUMENTS

| | | | | |
|---|---|---|---|---|
| 4,171,072 A  * | 10/1979 | Davis, Jr. ................. | 222/326 |
| 6,352,176 B1 * | 3/2002 | Hartsell et al. ............ | 222/1 |
| 6,986,441 B2 * | 1/2006 | Scordato et al. .......... | 222/63 |
| 2003/0022128 A1 * | 1/2003 | Heymann et al. ......... | 433/89 |

FOREIGN PATENT DOCUMENTS

| | | |
|---|---|---|
| DE | 199 51 504 A1 | 10/1999 |
| EP | 0 087 029 A1 | 2/1983 |
| EP | 0 087 029 A | 8/1983 |
| EP | 1 279 379 A1 | 7/2001 |

OTHER PUBLICATIONS

Search Report for Priority Application No. 10 2005 033 261.7 filed Jul. 15, 2005 in Germany.

* cited by examiner

*Primary Examiner* — Kevin P Shaver
*Assistant Examiner* — Andrew Bainbridge
(74) *Attorney, Agent, or Firm* — Alix, Yale & Ristas, LLP

(57) ABSTRACT

A method for producing a multicomponent compound involves pressing components out of cartridges by means of pistons. The method has particular applicability in connection with dental applications. The method prevents pressing the components initially under high pressures. At the beginning of the pressing-out process, a pressure lower than the characteristic pressing-out pressure of the components from the cartridges is employed. Feed speeds are adjusted to constant value as a function of the pressing-out behavior of the components which are compared with stored or calculated values for a known material.

12 Claims, 3 Drawing Sheets

METHOD AND DEVICE FOR PRODUCING A MULTICOMPONENT COMPOUND

BACKGROUND

The disclosure relates to a method for producing a multicomponent compound, in particular for dental purposes, by pressing its components out of cartridges by means of pistons, and by mixing the components. The disclosure also relates to a device for carrying out the method.

Various problems occur in the production of multicomponent compounds, in particular for dental purposes. On the one hand, the components must be pressed in precisely the right mixture ratio into a mixer where they are mixed and can then be discharged. If the two components are to be used in equal quantities, then cylinders with equal diameter could be used as cartridges, with the pistons then also being moved forwards at the same speed in order to press out the components. This can take place by means of a single drive. With a device of said type, it would also be possible to press out components in some other ratio if the cartridges or cylinders have different diameters. A better adaptation to different mixing ratios is however obtained if each of the pistons is provided with a separate drive (DE 199 51 504 A1). In this way, it is possible to obtain the desired mixing ratio if the cartridges are actually filled and the pistons bear against the components such that no air pocket is present there. If an air pocket of said type is present in one of the cartridges, then material would of course initially be driven only out of one cartridge when both drives are set in operation, while in the other cartridge, the air would initially be compressed and escape such that no material or in any case far too little material is discharged. For this problem, too, however, there is a solution which is disclosed and claimed in a patent application filed at the same time as the present application.

In all of said cases, however, the following problem always occurs. When the piston is pressed against the material, an abrupt pressure increase takes place. This is the case in particular when the piston is moved with increased speed for as long as there is still air present between the piston and the material which is to be dispensed. A result of this is that, at the start, the desired mixing ratio is not obtained.

An object is that of creating a method and a device of the type specified in the introduction, in which, even in cases in which the piston is initially moved with high speed, pressing out under an initially increased pressure is prevented.

A solution comprises that the pressing-out process, at the beginning thereof, takes place at a reduced pressure.

SUMMARY

In one advantageous embodiment, the load state of the drive motor of the piston or of the pistons is measured by means of its current consumption. If a rise in the current and therefore of the load state is detected, this means that the piston has reached the material and there is no longer an air pocket between the material and the piston. In order to then begin the pressing-out process with reduced pressure, not only is the feed movement of the piston stopped, but rather the piston is retracted a short distance. Only then does the normal feed movement, with which the material is to be pressed out, begin. In this way, it is prevented that the piston initially acts with the increased feed speed on the material which is to be pressed out.

In another advantageous embodiment, the determination of the load state takes place using mechanical means. For this purpose, the piston is advantageously connected by means of a spring to a drive rod. Said spring is compressed at the moment when the piston reaches the material. The compression of the spring can then advantageously be detected outside the cartridges of this advantageous embodiment in that the piston rod projects outward through the drive rod, so that it is possible outside the cartridge to detect that the piston rod is no longer moving or is moving only to a small extent even though the drive rod is still being driven. Said relative movement can for example be detected by means of a microswitch or by means of a light barrier, so that the load state is then detected and the piston can be retracted a distance in order to begin with the normal pressing-out.

The latter is in many cases, however, completely unnecessary. In this embodiment, the pressing-out of the material specifically at the start does not take place with the full force and speed at all, since the spring initially deflects. Said "soft start" has the advantage that the discharge does not begin abruptly and immediately with full force, which could lead to the non-uniform mixture at least at the start.

The piston can also be embodied as an element which is separate from the drive and which bears against the material which is to be pressed out. If the drive is driven against said element and comes into contact with the latter, then the piston is initially not moved on account of the static friction against the cylinder wall. It is then possible to detect the contact using mechanical or visual means without a pressure already being exerted on the material.

DETAILED DESCRIPTION OF THE PREFERRED EMBODIMENTS

Figure 1:
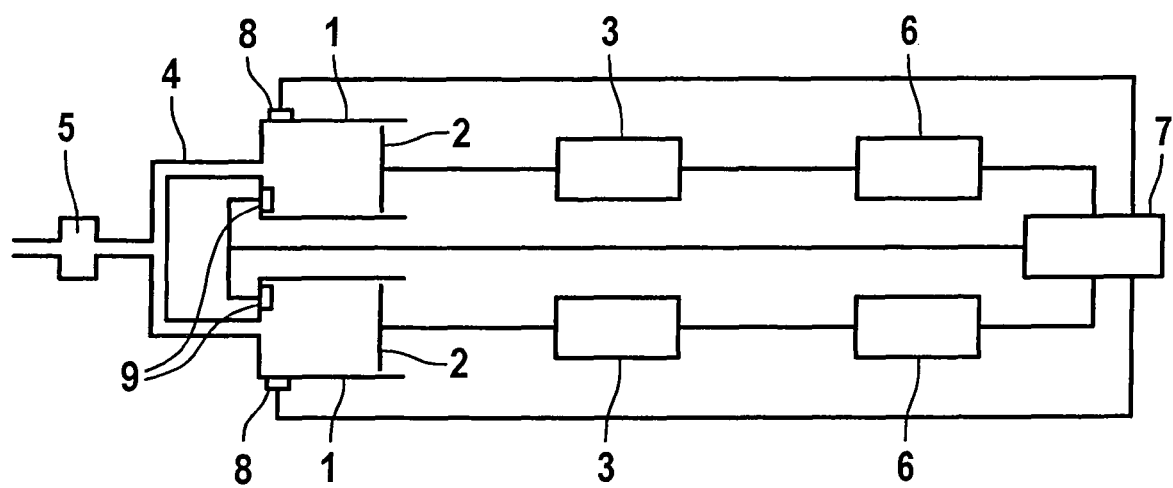
FIG. 1 schematically shows the construction of a device.

The device illustrated schematically in FIG. 1 has two cartridges or cylinders 1 in which is situated in each case one component. Arranged in said cylinders 1 are pistons 2 which are pressed into the cylinders 1 by means of drives 3 in order to feed the material via lines 4 into a mixer 5, where the components are mixed and then subsequently emerge from the mixer 5. The drives 3 are driven by means of units 6 with which the current consumption of the drives 3 is also measured. Here, the feed speeds of the pistons 2 are set by means of a controller 7 in such a way that said feed speeds assume constant values when the cylinders 1 are filled. If one or more of the cylinders 1 are only partially filled, then the feed speed of the corresponding piston 2 is increased until air pockets are eliminated and the actual pressing-out process can begin. The pressing-out behavior can be detected for example by means of pressure sensors 8 which detect the pressure or the deformation of the cylinders 1. Said signals can then be compared with values which are calculated or stored in the unit 7 in order to determine which components are situated in the cylinders 1 in order to set the optimum feed speeds for said components. The reference symbol 9 indicates yet further devices with which the emptying positions of the pistons can be detected in order that the pistons 2 can be moved back with increased speed in order that the cartridges 1 can be exchanged. By means of corresponding control with the unit 7, it is possible, according to the invention, to carry out the so-called "soft start". If the increased load state of a piston is detected (or of both pistons), said piston is first retracted slightly and only then is the pressing-out process started. The advantage is that the pressing-out process does not begin abruptly, which could result in the initial phase in a poor mixture ratio.

Said "soft start" is of course also possible in the case of devices which have more than two cylinders 1 or in which all cylinders 1 are driven by a common drive 3.

Figure 2:
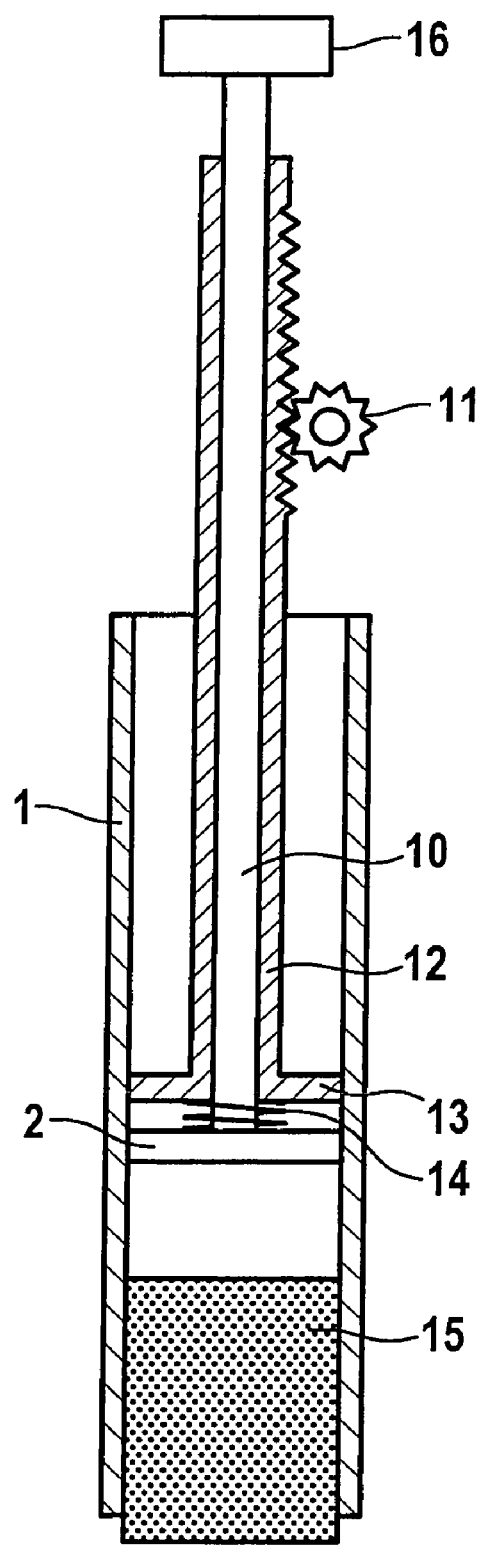
FIG. 2 shows a partial section of another advantageous embodiment.

FIG. 2 schematically illustrates another embodiment, specifically only one cartridge 1 with a piston 2, although the device according to the invention of course has a plurality of such cartridges 1 and pistons 2. Here, the drive takes place not to the piston rod 10 but rather via a gearwheel 11, which is connected to a drive (not shown), on a drive rod 12 which is of toothed-rack-like design in the upper part. The piston rod 10 is arranged, and guided so as to be axially movable, in said drive rod 12. Situated between a lower extension 13 of the rod and the piston 2 is a pressure spring 14. If the drive rod 12 is moved downwards by the drive gearwheel 11 and the piston 2 reaches the material 15, then the spring 14 is compressed. The relative movement between the drive rod 12 and the piston rod 10 can then be detected by means of a measuring device 16 which is arranged outside the cartridge 1. Said measuring device 16 can be a light barrier or a microswitch. On account of the action of the spring 14, it is thus possible to detect not only the load state. A "soft start" is in fact also obtained by virtue of the full force not acting on the material 15 immediately.

Figure 3:
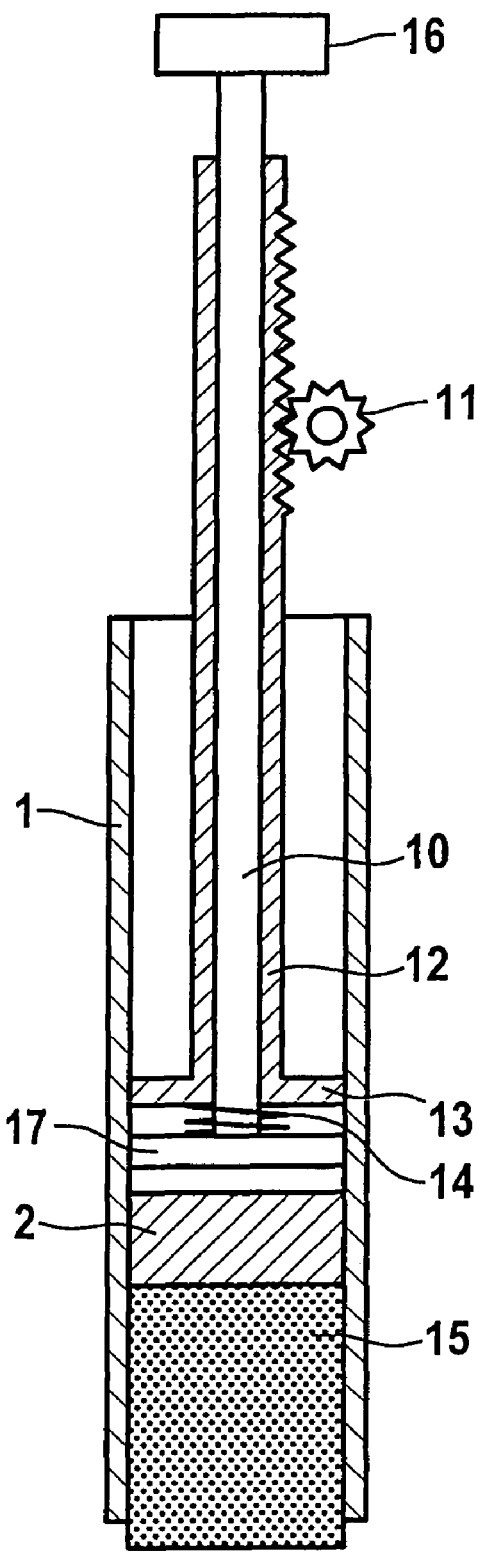
FIG. 3 shows a partial section of another embodiment, similar to the embodiment of FIG. 2.

FIG. 3 shows a case in which, in contrast to the embodiment of FIG. 2, the piston 2 is not directly connected to the drive 3, 10, 12, 13 but bears against the material 15. If the force transmission element 17 which is driven by the drive moves towards the piston 2 and comes into contact with the latter, then the piston 2 is initially not moved on account of the static friction against the cylinder wall, and also does not exert any pressure on the material 15. On account of the static friction of the piston 2 against the wall of the cylinder 1, however, the spring 14 is already compressed. The start of the load state is therefore detected without pressure already being exerted on the material 15. Although the force transmission element 17 is illustrated in the shape of a piston in FIG. 3, it can however of course also have other shapes which permit the function of force transmission.

The invention claimed is:

1. A method for producing a multicomponent compound by pressing its components out of cartridges by means of pistons in a pressing-out process and by mixing the components, characterized in that each piston has a feed movement at a plurality of speeds produced by a drive having a load state and the piston moves without contacting a component in a cartridge until the piston initially contacts the component in a relatively low contact force, and at the beginning of the pressing-out process, the cartridge component is pressed out with a low pressing-out pressure, and the cartridge component is subsequently pressed out at a relatively high pressing-out pressure.

2. The method as claimed in claim 1, characterized in that the load state of the drive is measured, in the event of an increase of the load state, the feed movement is ended, the piston is retracted a short distance and only then is the feed movement for the normal pressing-out process started.

3. The method as claimed in claim 2, characterized in that the drive is powered by electric current consumption and the load state of the drive is detected by measuring the current consumption.

4. The method as claimed in claim 2, characterized in that the load state of the drive is determined using mechanical means.

5. The method as claimed in claim 1, characterized in that the components have a pressing-out behavior and an adjustment of the feed speeds to constant values takes place as a function of the pressing-out behavior of the components, which is compared with stored or calculated values for known materials.

6. The method as claimed in claim 1, in which the components are mixed with a dynamic mixer after being pressed out of the cartridges, characterized in that the mixer is driven first from the moment at which one or more pistons reach the load state.

7. The method as claimed in claim 2, characterized in that the components have a pressing-out behavior and an adjustment of the feed speeds to constant values takes place as a function of the pressing-out behavior of the components, which is compared with stored or calculated values for known materials.

8. The method as claimed in claim 3, characterized in that the components have a pressing-out behavior and an adjustment of the feed speeds to constant values takes place as a function of the pressing-out behavior of the components, which is compared with stored or calculated values for known materials.

9. The method as claimed in claim 4, characterized in that the components have a pressing-out behavior and an adjustment of the feed speeds to constant values takes place as a function of the pressing-out behavior of the components, which is compared with stored or calculated values for known materials.

10. The method as claimed in claim 2, in which the components are mixed with a dynamic mixer after being pressed out of the cartridges, characterized in that the mixer is driven first from the moment at which one or more pistons reach the load state.

11. The method as claimed in claim 3, in which the components are mixed with a dynamic mixer after being pressed out of the cartridges, characterized in that the mixer is driven first from the moment at which one or more pistons reach the load state.

12. The method as claimed in claim 4, in which the components are mixed with a dynamic mixer after being pressed out of the cartridges, characterized in that the mixer is driven first from the moment at which one or more pistons reach the load state.

* * * * *